（12）United States Patent
Liu

(10) Patent No.: US 11,647,788 B2
(45) Date of Patent: May 16, 2023

(54) ELECTRONIC CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 327 days.

(21) Appl. No.: 17/013,815

(22) Filed: Sep. 7, 2020

(65) Prior Publication Data

US 2021/0186106 A1  Jun. 24, 2021

(30) Foreign Application Priority Data

Dec. 19, 2019 (CN) .......................... 201922303416.1

(51) Int. Cl.
*A24F 40/10* (2020.01)
*A24F 40/40* (2020.01)
*A24F 40/42* (2020.01)
*A24F 40/46* (2020.01)

(52) U.S. Cl.
CPC .............. *A24F 40/46* (2020.01); *A24F 40/10* (2020.01); *A24F 40/42* (2020.01)

(58) Field of Classification Search
CPC .......... A24F 40/10; A24F 40/40; A24F 40/42; A24F 40/46; A61M 11/042; A61M 15/06; A61M 2205/3375; A61M 2205/8206
See application file for complete search history.

(56) References Cited

U.S. PATENT DOCUMENTS

| | | | |
|---|---|---|---|
| 10,219,546 B2 * | 3/2019 | Li | A24F 40/485 |
| 11,202,469 B2 * | 12/2021 | Chen | H01R 31/06 |
| 2017/0156400 A1 * | 6/2017 | Liu | H05B 3/46 |
| 2017/0196264 A1 * | 7/2017 | Liu | A24F 40/60 |
| 2019/0142069 A1 * | 5/2019 | Qiu | A24F 40/485 |
| | | | 131/329 |
| 2020/0359702 A1 * | 11/2020 | Cheng | H05B 1/0297 |

* cited by examiner

*Primary Examiner* — Abdullah A Riyami
*Assistant Examiner* — Thang H Nguyen
(74) *Attorney, Agent, or Firm* — Matthias Scholl P.C.; Matthias Scholl

(57) ABSTRACT

An electronic cigarette, including an atomization part and a battery part. The atomization part and the battery part are disposed side by side in the electronic cigarette thereby preventing the e-liquid in the atomization part from flowing into the battery part.

2 Claims, 3 Drawing Sheets

ELECTRONIC CIGARETTE

CROSS-REFERENCE TO RELATED APPLICATIONS

Pursuant to 35 U.S.C. § 119 and the Paris Convention Treaty, this application claims foreign priority to Chinese Patent Application No. 201922303416.1 filed Dec. 19, 2019, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to an electronic cigarette.

A conventional electronic cigarette includes an atomization part and a battery part. The atomization part is disposed on the battery part. When the electronic cigarette leaks, the e-liquid in the atomization part flows into the battery part. This leads to the risk of short circuit.

SUMMARY

The disclosure provides an electronic cigarette comprising an atomization part and a battery part; the atomization part and the battery part are disposed side by side in the electronic cigarette thereby preventing the e-liquid in the atomization part from flowing into the battery part.

The electronic cigarette further comprises a bottom cover; the bottom cover comprises a recess configured to accommodate e-liquid condensate thereby preventing the e-liquid from flowing out of the electronic cigarette; the atomization part comprises a first strip of cotton for filtering vapor and absorbing a condensate.

The atomization part further comprises a first silicone seal, a seal cover, a seal ring, a second strip of cotton, an e-liquid storage tube, a first fiber tube, a second fiber tube shorter than the first fiber tube, a heating wire, and a second silicone seal; the heating wire is horizontally fixed on the first fiber tube; the second fiber tube is disposed around the first fiber tube; the first fiber tube is fixedly disposed on the second silicone seal; the second silicone seal is disposed on a first end of the e-liquid storage tube thereby sealing a first opening of the e-liquid storage tube; and the second strip of cotton is wrapped around the first fiber tube.

The seal ring is disposed around the seal cover; the seal cover is disposed on a second end of the e-liquid storage tube thereby sealing a second opening of the e-liquid storage tube; the first silicone seal is disposed on the seal cover; and the first strip of cotton is disposed on the first silicone seal for filtering vapor and absorbing condensate.

The battery part comprises a silicone pad, a pneumatic switch, and a battery; the battery comprises positive and negative terminals connected to the pneumatic switch to supply power to the pneumatic switch; the pneumatic switch is disposed in the silicone pad; the silicone pad is fixedly disposed on the seal cover.

The atomization part and the battery part are disposed side by side in the electronic cigarette thereby preventing the e-liquid in the atomization part from flowing into the battery part. The bottom cover comprises a recess configured to accommodate e-liquid condensate thereby preventing the e-liquid from flowing out of the electronic cigarette. The first strip of cotton of the atomization part filters the vapor and absorbs the e-liquid condensate.

DETAILED DESCRIPTION

To further illustrate, embodiments detailing an electronic cigarette are described below. It should be noted that the following embodiments are intended to describe and not to limit the disclosure.

Figure 1:
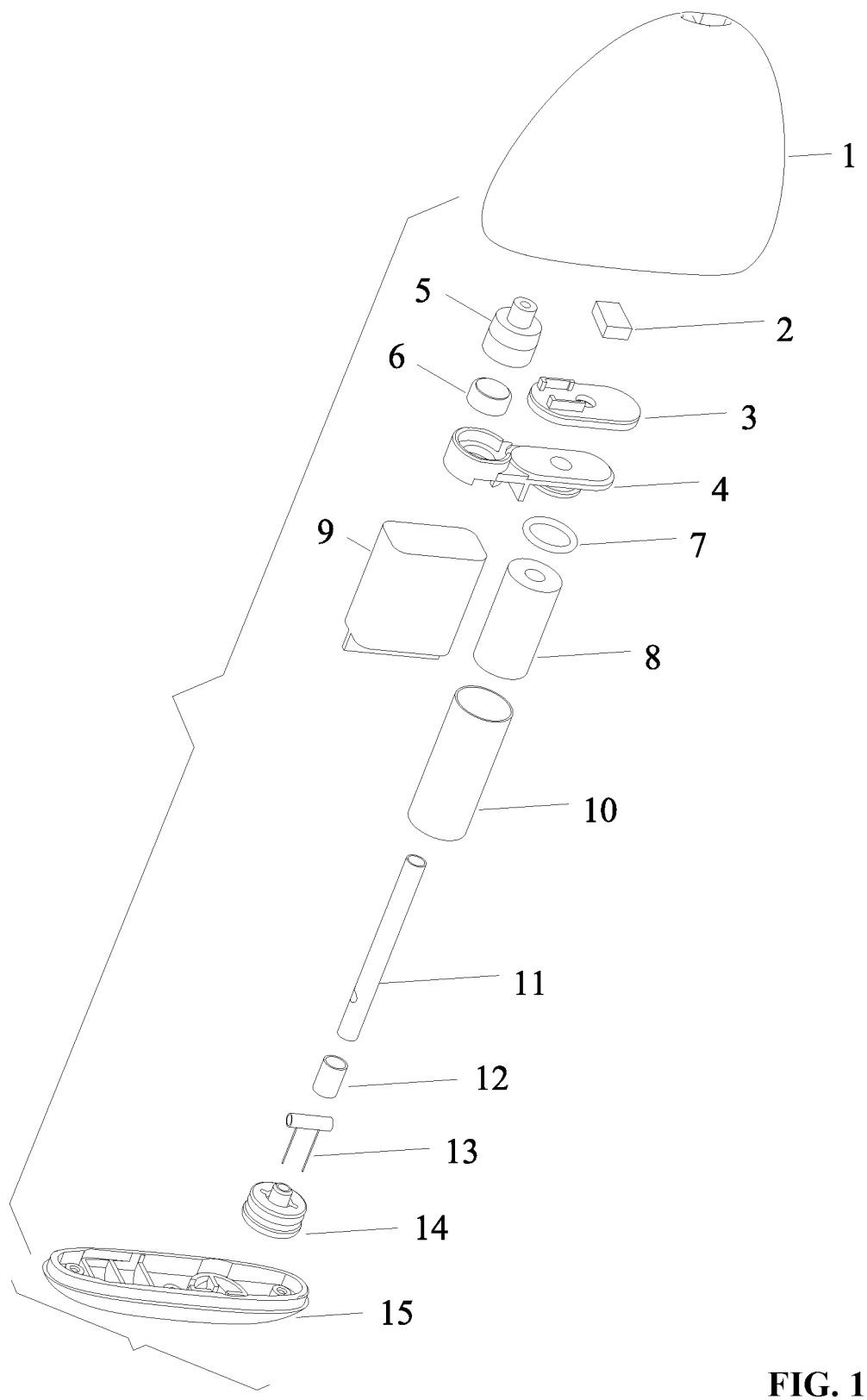
FIG. 1 is an exploded view of an electronic cigarette according to one embodiment of the disclosure.
Figure 2:
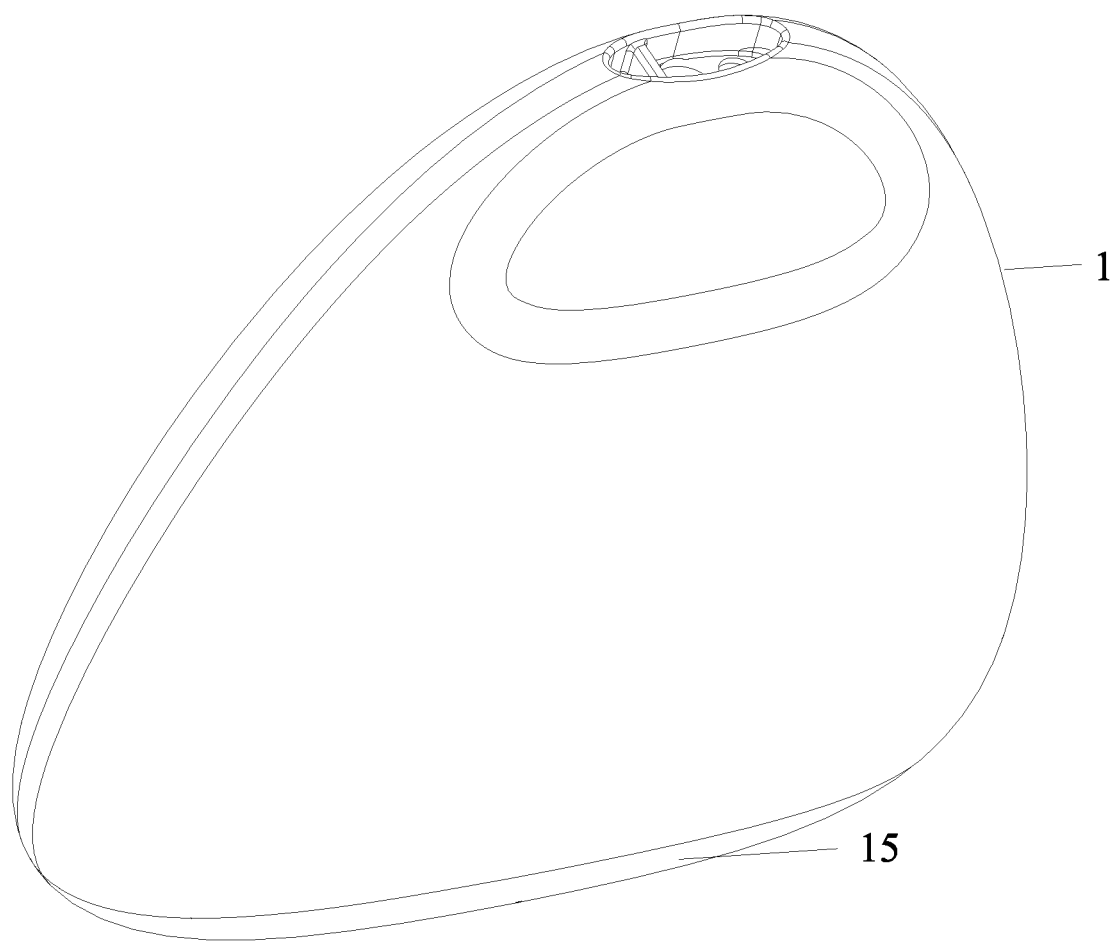
FIG. 2 is a schematic diagram of an electronic cigarette according to one embodiment of the disclosure.
Figure 3:
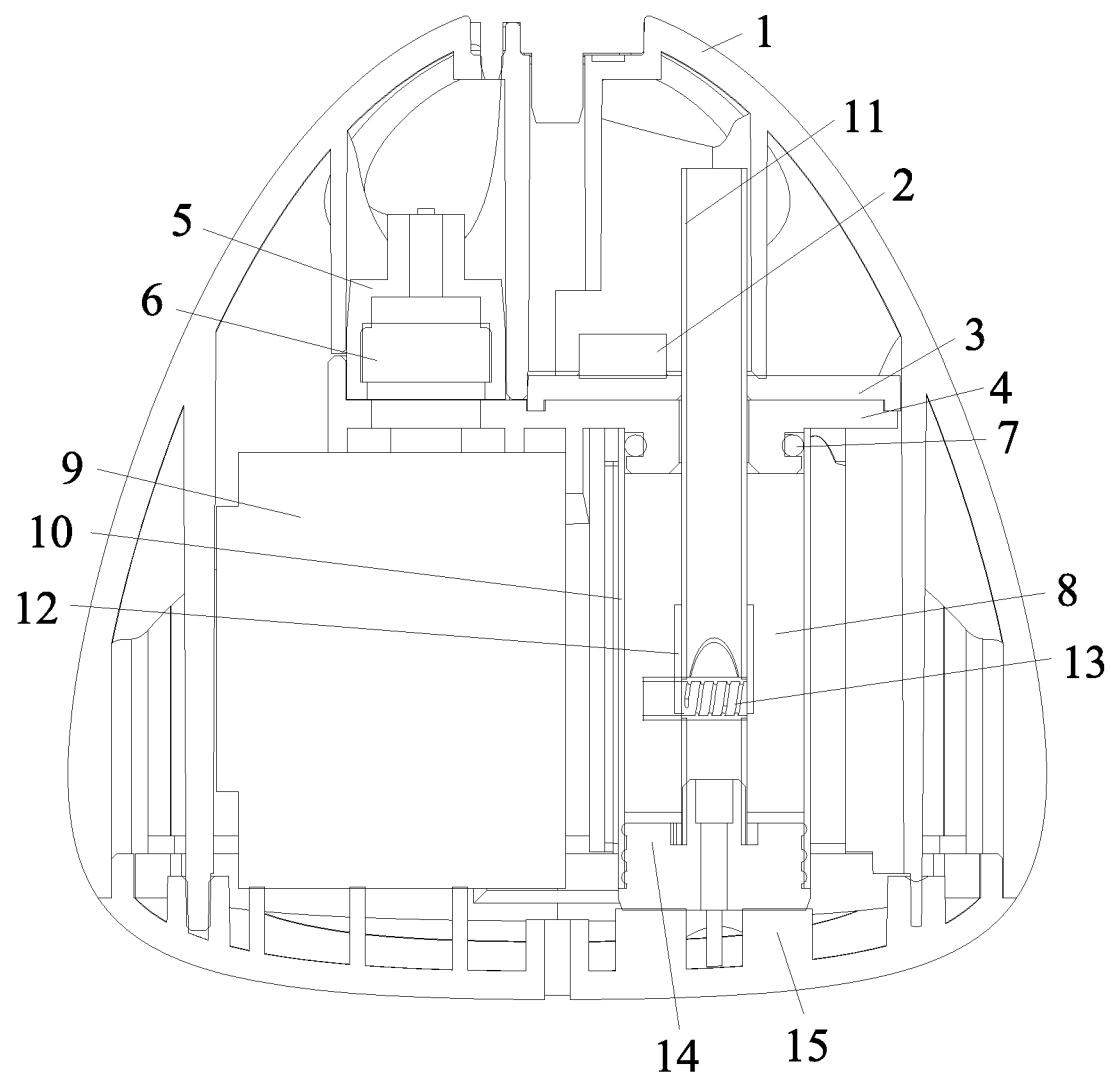
FIG. 3 is a sectional view of an electronic cigarette according to one embodiment of the disclosure.

As shown in FIGS. 1-3, an electronic cigarette comprises an atomization part and a battery part. The atomization part and the battery part are disposed side by side in the electronic cigarette. Specifically, the electronic cigarette comprises a mouthpiece 1, a first strip of cotton 2, a first silicone seal 3, a seal cover 4, a silicone pad 5, a pneumatic switch 6, a seal ring 7, a second strip of cotton 8, a battery 9, an e-liquid storage tube 10, a first fiber tube 11, a second fiber tube 12 shorter than the first fiber tube, a heating wire 13, a second silicone seal 14, and a bottom cover 15. The heating wire 13 is horizontally fixed on the first fiber tube 11; the second fiber tube 12 is disposed around the first fiber tube 11; the first fiber tube 11 is fixedly disposed on the second silicone seal 14; the second silicone seal 14 is disposed on a first end of the e-liquid storage tube 10 thereby sealing a first opening of the e-liquid storage tube 10; and the second strip of cotton 8 is wrapped around the first fiber tube 11. The seal ring 7 is disposed around the seal cover 4; the seal cover 4 is disposed on a second end of the e-liquid storage tube 10 thereby sealing a second opening of the e-liquid storage tube 10; the first silicone seal 3 is disposed on the seal cover 4; and the first strip of cotton 2 is disposed on the first silicone seal 3 for filtering vapor and absorbing condensate. The battery part comprises a silicone pad 5, a pneumatic switch 6, and a battery 9; the battery comprises positive and negative terminals connected to the pneumatic switch to supply power to the pneumatic switch; the pneumatic switch 6 is disposed in the silicone pad; the silicone pad 5 is fixedly disposed on the seal cover 4. The atomization part is disposed in the left side of the electronic cigarette, and the battery part is disposed in the right side of the electronic cigarette, thereby preventing the e-liquid in the atomization part from flowing into the battery part. The bottom cover 15 is disposed at the bottom of the mouthpiece 1 for collecting e-liquid condensate in the electronic cigarette.

The bottom cover 15 comprises a recess configured to accommodate e-liquid condensate thereby preventing the e-liquid from flowing out of the electronic cigarette. The first strip of cotton 2 of the atomization part is configured to filter vapor and absorb the e-liquid condensate.

The following advantages are associated with the electronic cigarette of the disclosure.

1. The atomization part and the battery part are disposed side by side in the electronic cigarette thereby preventing the e-liquid in the atomization part from flowing into the battery part.

2. The bottom cover comprises a recess configured to accommodate e-liquid condensate thereby preventing the e-liquid from flowing out of the electronic cigarette.

3. The first strip of cotton of the atomization part filters the vapor and absorbs the e-liquid condensate.

It will be obvious to those skilled in the art that changes and modifications may be made, and therefore, the aim in the appended claims is to cover all such changes and modifications.

What is claimed is:

1. An electronic cigarette, comprising an atomization part, and a battery part, wherein:
   the atomization part and the battery part are disposed side by side in the electronic cigarette thereby preventing e-liquid in the atomization part from flowing into the battery part;
   the atomization part comprises a first strip of cotton, a first silicone seal, a seal cover, a seal ring, a second strip of cotton, an e-liquid storage tube, a first fiber tube, a second fiber tube shorter than the first fiber tube, a heating wire, and a second silicone seal;
   the heating wire is horizontally fixed on the first fiber tube;
   the second fiber tube is disposed around the first fiber tube;
   the first fiber tube is fixedly disposed on the second silicone seal;
   the second silicone seal is disposed on a first end of the e-liquid storage tube thereby sealing a first opening of the e-liquid storage tube;
   the second strip of cotton is wrapped around the first fiber tube;
   the seal ring is disposed around the seal cover;
   the seal cover is disposed on a second end of the e-liquid storage tube thereby sealing a second opening of the e-liquid storage tube;
   the first silicone seal is disposed on the seal cover; and
   the first strip of cotton is disposed on the first silicone seal for filtering vapor and absorbing condensate.

2. The electronic cigarette of claim 1, wherein the battery part comprises a silicone pad, a pneumatic switch, and a battery; the battery is connected to the pneumatic switch to supply power to the pneumatic switch; the pneumatic switch is disposed in the silicone pad; the silicone pad is fixedly disposed on the seal cover.

* * * * *